US 7,355,692 B2

United States Patent
Noy et al.

(10) Patent No.: US 7,355,692 B2
(45) Date of Patent: Apr. 8, 2008

(54) SYSTEM AND METHOD FOR INSPECTING ELECTRICAL CIRCUITS UTILIZING REFLECTIVE AND FLUORESCENT IMAGERY

(75) Inventors: Amir Noy, Kfar Mordehai (IL); Gilad Davara, Rehovot (IL)

(73) Assignee: Orbotech Ltd, Yavne (IL)

( * ) Notice: Subject to any disclaimer, the term of this patent is extended or adjusted under 35 U.S.C. 154(b) by 338 days.

(21) Appl. No.: 10/793,224

(22) Filed: Mar. 5, 2004

(65) Prior Publication Data

US 2005/0195389 A1    Sep. 8, 2005

(51) Int. Cl.
*G01J 1/10* (2006.01)
(52) U.S. Cl. .................................. 356/237.5
(58) Field of Classification Search ............. 356/237.2, 356/237.3, 237.4, 237.5, 237.1, 239.8
See application file for complete search history.

(56) References Cited

U.S. PATENT DOCUMENTS

| 4,692,690 | A | * | 9/1987 | Hara et al. .................. 356/394 |
| 4,877,326 | A | * | 10/1989 | Chadwick et al. .......... 356/394 |
| 5,774,572 | A | | 6/1998 | Caspi |
| 5,774,573 | A | | 6/1998 | Caspi et al. |
| 2003/0020905 | A1 | | 1/2003 | Savareigo et al. |
| 2003/0174877 | A1 | | 9/2003 | Aiger |

FOREIGN PATENT DOCUMENTS

| WO | WO 0026645 | 5/2000 |
| WO | WO 0111565 | 2/2001 |
| WO | WO 0188592 | 11/2001 |

OTHER PUBLICATIONS

Brochure: *INSPIRE-9055™ Automated AOI system*, Orbotech Ltd., Yavne, Israel, Jan. 2003.
Brochure: *VRS-F™ Series*, Orbotech Ltd., Yavne, Israel, Feb. 2003.
Brochure: *InFinex-3000™ Series*, Orbotech Ltd., Yavne, Israel, Apr. 2003.
Brochure: *SPIRON-8800™ Series with Revolutionary VIP™ Technology*, Orbotech Ltd., Yavne, Israel, Feb. 2003.

* cited by examiner

*Primary Examiner*—Hwa (Andrew) Lee
(74) *Attorney, Agent, or Firm*—Sughrue Mion, PLLC

(57) ABSTRACT

A method for inspecting an electrical circuit including optically inspecting at least a portion of an electrical circuit by detecting light reflected therefrom in a first image during a first time interval, optically inspecting light emitted from at least a portion of the electrical circuit by fluorescence in a second image acquired during a second time interval and indicating defects in the electrical circuit based on geometrically coincident indications from both the optically inspecting at least a portion of an electrical circuit by detecting light reflected therefrom and the optically inspecting light emitted from at least a portion of the electrical circuit by fluorescence.

39 Claims, 5 Drawing Sheets

SYSTEM AND METHOD FOR INSPECTING ELECTRICAL CIRCUITS UTILIZING REFLECTIVE AND FLUORESCENT IMAGERY

FIELD OF THE INVENTION

The present invention relates to the inspection of electrical circuits during manufacture generally and more particularly to the reduction of misdetection of non-defects during the inspection of printed circuit boards.

BACKGROUND OF THE INVENTION

Various automated optical inspection (AOI) systems are commercially available to inspect electrical circuits, such as printed circuit boards, during manufacture to detect defects. Some AOI systems acquire an image of an electrical circuit to be inspected with reflected monochromatic or polychromatic light. Reflected light AOI systems include the Inspire™, Spiron™ and InFinex™ AOI systems available from Orbotech Ltd. of Yavne, Israel. Other AOI systems acquire an image of an electrical circuit to be inspected from a fluorescence response to a scanned laser beam. Scanning laser AOI systems include the Vision™ AOI system also available from Orbotech Ltd. of Yavne, Israel.

In order to ensure that all defects on an electrical circuit are detected, AOI systems are adjusted to produce a detection result sufficiently sensitive to detect all real defects. Such a level of sensitization also results in some non-defective locations being falsely identified as including a defect. Accordingly, after inspection defects identified during AOI are verified in a downstream verification operation to confirm whether the defect is indeed a real defect, or rather a false call.

SUMMARY OF THE INVENTION

The present invention seeks to provide improved systems and methodologies for the inspection of electrical circuits for defects.

The present invention further seeks to provide an improved AOI system operative to inspect both reflectance and fluorescence images of an electrical circuit, the reflectance and fluorescence images being acquired during different time intervals.

There is thus provided in accordance with a preferred embodiment of the present invention a method for inspecting an electrical circuit including optically inspecting at least a portion of an electrical circuit by detecting light reflected therefrom in a first image during a first time interval and optically inspecting light emitted from at least a portion of the electrical circuit by fluorescence in a second image acquired during a second time interval and indicating defects in the electrical circuit based on geometrically coincident indications from both the optically inspecting at least a portion of an electrical circuit by detecting light reflected therefrom and the optically inspecting light emitted from at least a portion of the electrical circuit by fluorescence.

There is also provided in accordance with another preferred embodiment of the present invention apparatus for inspecting an electrical circuit including reflective inspection functionality operative to optically inspect at least a portion of an electrical circuit by detecting light reflected therefrom, fluorescence inspection functionality operative to optically inspect light emitted from at least a portion of the electrical circuit by fluorescence and a defect indicator operative to indicate defects in the electrical circuit based on geometrically coincident indications from both the reflective inspection functionality and the fluorescence inspection functionality.

Further embodiments of the present invention include one or more of the following additional features and functionalities.

The electrical circuit is scanned using reflected light.

The electrical circuit is inspected with fluorescence imagery generally only at regions indicated to possibly contain defects by the reflective inspection.

The fluorescence inspection includes illuminating a portion of the electrical circuit with light having a wavelength of less than 420 nm, preferably of about 410 nm.

The inspection includes comparing a portion of the second image, corresponding to a location on the first image of a potential defect, to a reference. The comparing may include extracting first contours from the second image and comparing the first contours to second contours obtained from the reference.

The acquiring of a high quality reflectance image of the electrical circuit for at least one of: a defect and a candidate defect not conclusively determined to be a misdetection and evaluating the high quality reflectance image to make a further defect determination.

The reflectance and fluorescent images are acquired one after the other during scanning an electrical circuit to be inspected, for example using a scanned camera acquiring two dimensional images, the electrical circuit being illuminated with suitable flash illumination during image acquisition.

BRIEF DESCRIPTION OF THE DRAWINGS

The present invention will be understood and appreciated more fully from the following detailed description, taken in conjunction with the drawings in which.

DETAILED DESCRIPTION

Figure 1:
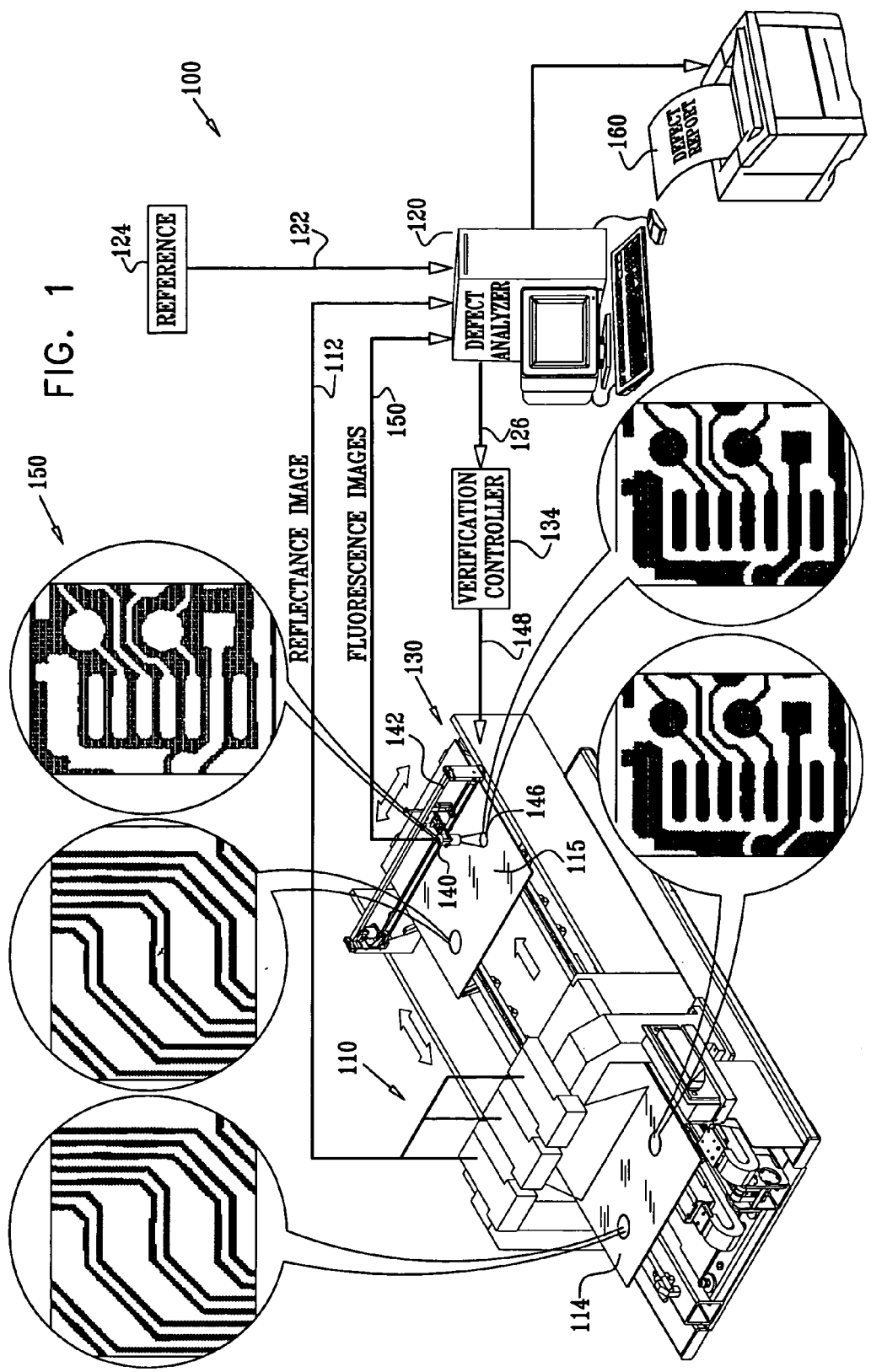
FIG. 1 is a simplified pictorial illustration of apparatus and a functionality for inspecting an electrical circuit in accordance with an embodiment of the present invention.

Reference is made to FIG. 1, which is a simplified pictorial illustration of apparatus and a functionality for inspecting an electrical circuit in accordance with an embodiment of the present invention. In accordance with an embodiment of the invention, an AOI system 100 includes at least a first inspection station 110 acquiring an image including at least one or more reflectance images 112 of a first electrical circuit to be inspected, designated reference numeral 114.

A reflectance image 112 is acquired, for example, by scanning first electrical circuit 114. Optionally, reflectance image 112 may be a composite of a plurality of two dimensional image frames of electrical circuit 114. Different reflectance images may be acquired under the same, or different, configurations of illumination. In accordance with an embodiment of the present invention, AOI system 100 is a Spiron™ AOI system, commercially available from Orbotech Ltd., suitably adapted to perform automated optical inspection of a reflectance image, and then to verify candidate defects by optically inspecting an inspection verification image obtained from fluorescence.

As seen in FIG. 1, a reflectance image 112 is provided to a defect analyzer 120 operative to additionally receive a reference image 122 prepared, for example, from a computer file reference 124, corresponding to first electrical circuit 114. Suitable computer file references may be derived from CAM files and images acquired from printed circuit boards which are known to be not defective. In accordance with an embodiment of the invention, computer file reference 124 comprises a binary image. Optionally, computer file reference 124 comprises a map of contours, namely edges between conductor and substrate, corresponding to an electrical circuit to be inspected.

Defect analyzer 120 is operative to automatically optically inspect reflectance image 112 and to output indications of candidate defects 126 on an electrical circuit 114. Upon completion of optical inspection, an electrical circuit is passed down stream to a verification station 130. From FIG. 1, it is noted that a first electrical circuit 114 undergoing automated optical inspection is located at inspection station 110, while a second previously inspected electrical circuit 115 is located at verification station 130. Previously inspected electrical circuit 115 has already been automatically optically inspected at inspection station 110, and at least one candidate defect thereon has been identified by defect analyzer 120. The locations of candidate defects on an electrical circuit 115 typically are different from those found on other electrical circuits inspected at the same time, although some of the candidate defects may be similar and may recur at the location on successive electrical circuits of the same type.

The indications of candidate defects 126 (corresponding to candidate defects identified on previously inspected electrical circuit 115) are received by a verification controller 134, which is in operative communication with verification station 130. Verification station 130 may be integrally formed on the same chassis as first inspection 110, as seen in FIG. 1. A system integrally combining an inspection station 110 and a verification station 130 is the Spiron™ AOI system commercially available from Orbotech Ltd. Optionally, verification station 130 may be a stand alone verification station, for example a VRS-5™ verification and repair station, also commercially available from Orbotech Ltd. of Yavne, Israel, operative downstream of a stand alone automatic optical inspection station, for example an Inspire™ AOI system, also commercially available from Orbotech Ltd. In accordance with yet another embodiment of the invention, reflectance images and fluorescence images are obtained sequentially during scanning of an electrical circuit with an area camera. For example, the configuration of flash illumination is sequentially changed while scanning the area camera. In this manner multiple collections of images are acquired. Each collection covers the entire electrical circuit, but is illuminated with one of at least two different configurations of illumination that are used during image acquisition.

In accordance with an embodiment of the invention, verification station 130 includes a camera 140 and a positioner 142 operative to sequentially position camera 140 to sequentially view locations of candidate defects 146 according to an output 148 of verification controller 134. Output 148 provides the geometric location of candidate defects as identified by defect analyzer 120. In the embodiment seen in FIG. 1, positioner 142 is operative to independently control an X-Y positioning of camera 140.

At each sequentially viewed candidate defect location 146, on an inspected electrical circuit 115, the location 146 is illuminated with light suitable to provide an image suitable to be utilized for an additional automatic computerized defect analysis. In accordance with an embodiment of the invention, candidate defect location 146 is illuminated with light at a wavelength that causes a substrate portion thereat to fluoresce. Optionally, other suitable forms of illumination may be employed, for example polychromatic light provided at a grazing angle.

In accordance with an embodiment of the invention, camera 140 acquires a fluorescence image 150 of the fluorescence response. The fluorescence image 150 is acquired during a time interval separate from the time interval during which a reflectance image 112 is acquired. Thus, for example, in accordance with an embodiment of the invention, fluorescence images 150 are acquired only after the entire electrical circuit 115 is scanned and at least one reflectance image is acquired for all of the electrical circuit 115, although this need not be the case. In the embodiment seen in FIG. 1, upon acquisition of a fluorescence image 150, camera 140 is repositioned at a next candidate defect, the location of which is provided by output 148, and a fluorescence image is acquired at that location. The fluorescence images 150, at least one image for each candidate defect location, are provided to defect analyzer 120, which automatically analyzes each fluorescence image to verify whether a candidate defect is an actual defects or rather a misdetection of a non-defect, sometimes referred to as a false call. Optionally, AOI system 100 is operative to acquire both reflectance image 112 and fluorescence image 150 in a plurality of separate time intervals during scanning, for example as a plurality of temporally offset images acquired with one of selected different types of illumination.

In the embodiment seen in FIG. 1, it is seen that defect analyzer is operative to provide an image analysis functionality for both the reflectance image acquired during initial inspection and an additional image, such as a fluorescence image, acquired during automatic verification. These functionalities may be provided using the same processor in the same computer, as seen in FIG. 1, using separate processors within the same computer, or using separate processors using separate computers. The image analysis functionalities for initial inspection and subsequent automatic verification may utilize at least some image processing algorithms that are the same, or they may utilize image processing algorithms that are different.

In accordance with an embodiment of the invention, upon further analysis of each fluorescence image 150, defect analyzer outputs a defect report 160 indicating actual defects on an electrical circuit that has been initially optically inspected at least in part using reflected light, and for which candidate defects have been further optically inspected to verify candidate defects as being actual defects utilizing fluorescence imaging. Each indication of an actual defect is based on geometric coincidence of a candidate defect location as determined from optically inspecting at least a reflectance image, and from further optically inspecting a fluorescence image corresponding to the same location.

Figure 2:
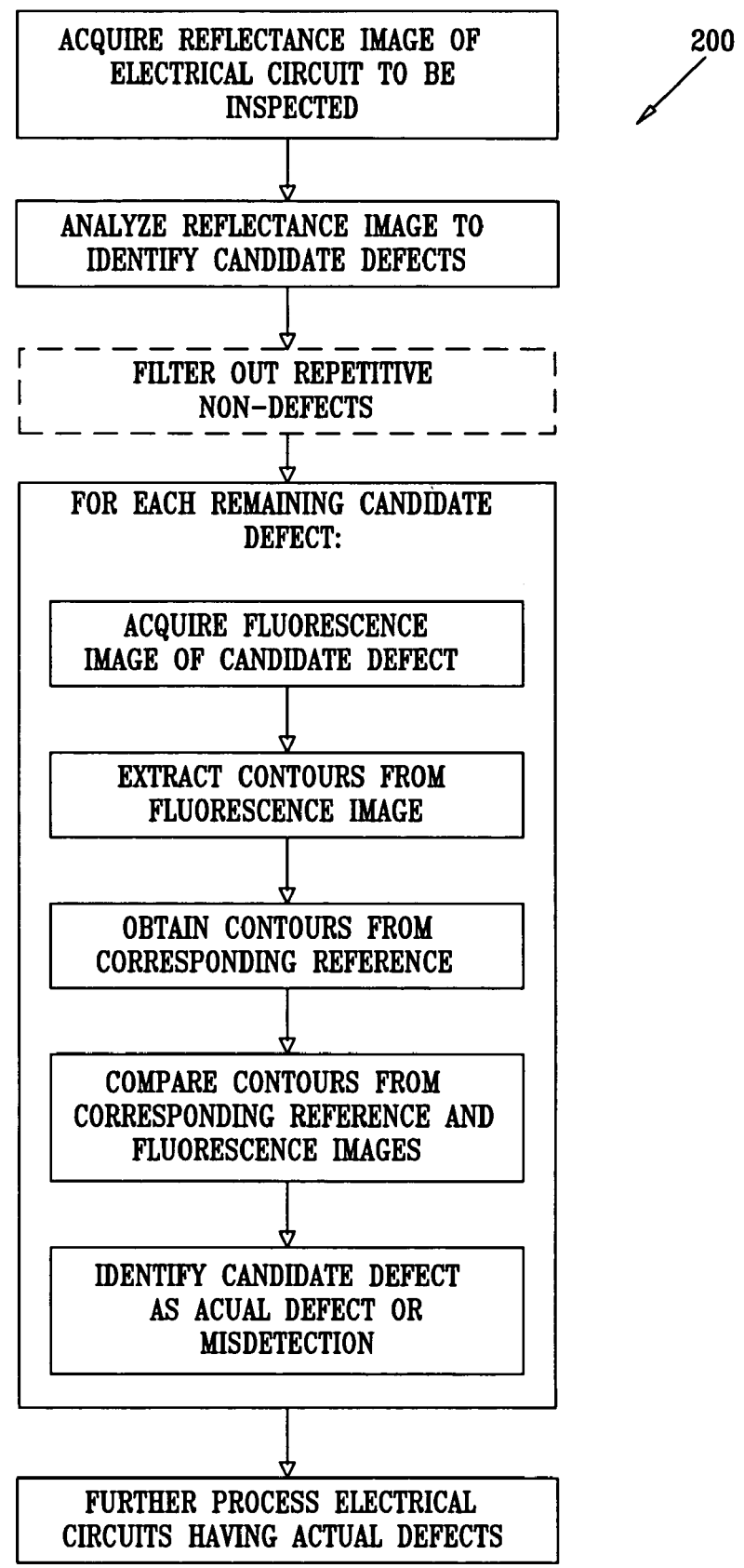
FIG. 2 is a simplified flow diagram of a method for inspecting electrical circuits utilizing the apparatus and functionality of FIG. 1.
Figure 3A:
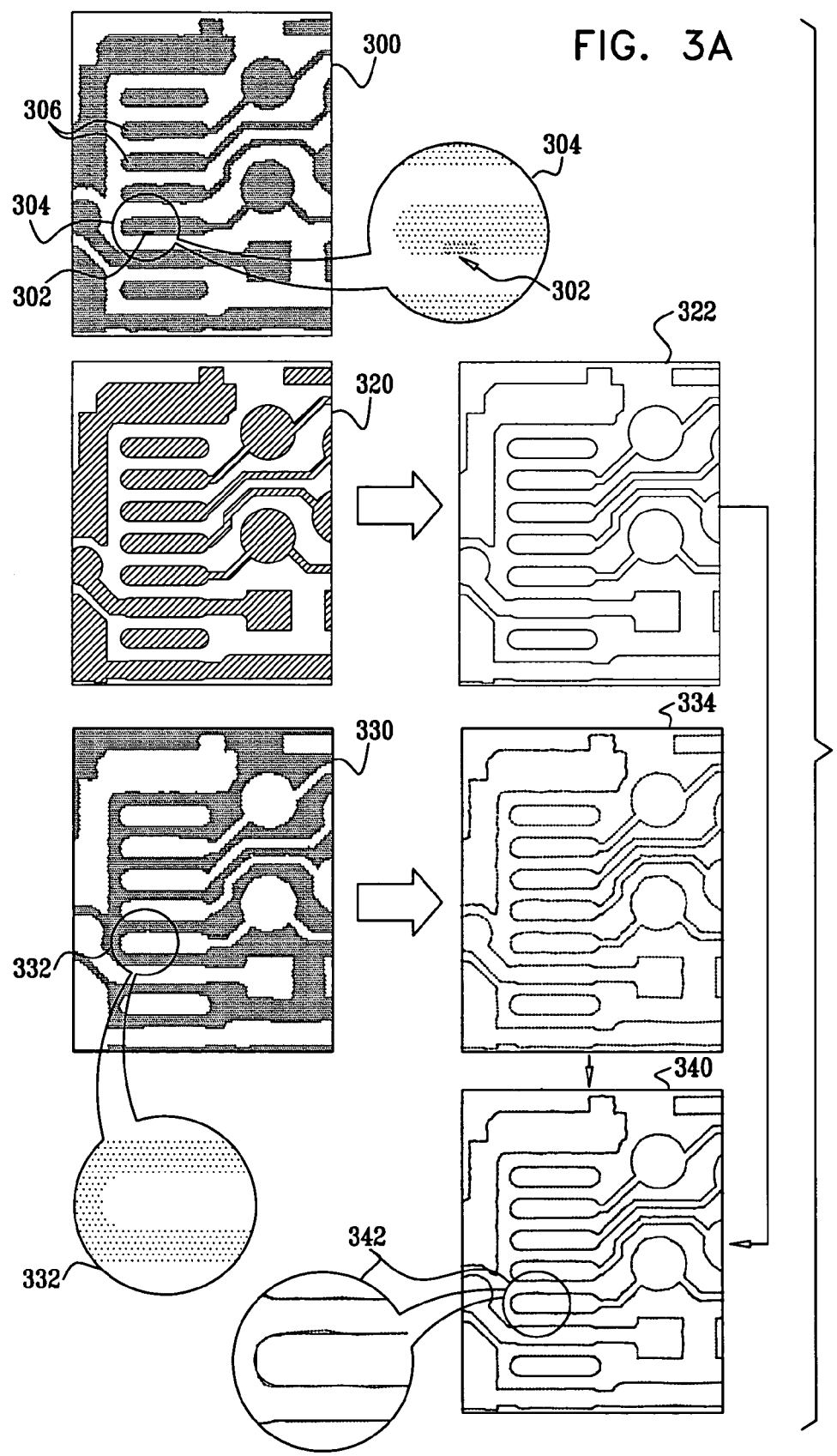
FIGS. 3A and 3B are schematic illustrations of inspection results from inspecting an electrical circuit, illustrating the method of FIG. 2.
Figure 3B:
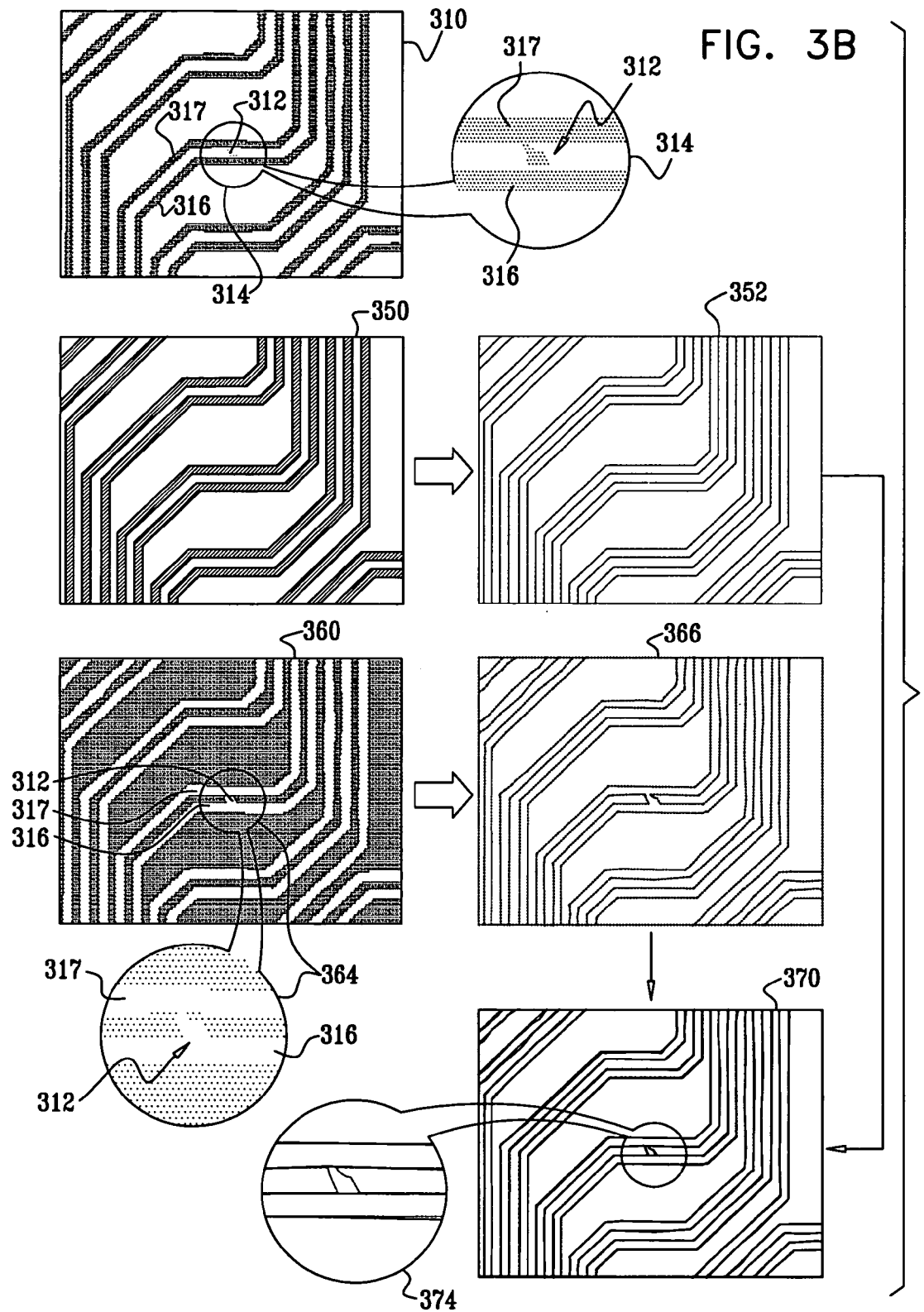

Reference is now made to FIG. 2, which is a simplified flow diagram 200 of a method for inspecting electrical circuits utilizing the apparatus and functionality of FIG. 1, and to FIGS. 3A and 3B which are schematic illustrations of inspection results from inspecting an electrical circuit, illustrating the method of FIG. 2 for two different types of candidate defects.

In accordance with an embodiment of the invention, a reflectance image of an electrical circuit to be inspected is acquired, for example at inspection station 110 in FIG. 1. The reflectance image is automatically optically inspected and analyzed, for example at defect analyzer 120, to detect candidate defects in the electrical circuit to be inspected. At this stage, various defects have been identified, however it still needs to be verified whether the defects are actual defects or misdetections or false calls.

An automated optical inspection operation using a reflectance image is illustrated, for two different types of possible defects, in FIGS. 3A and 3B respectively. Image frame 300 in FIG. 3A illustrates a reflectance image corresponding to a portion of an electrical circuit having a discoloration, such as from oxidation 302, at a candidate defect location 304. Oxidation reflects light differently than surrounding metal conductors 306. In systems employing reflective light, a conductor which is partially oxidized may be misinterpreted by automated optical inspection as being malformed and defective. Following automated optical inspection using reflective light, location 304 is indicated as a candidate defect.

Image frame 310 in FIG. 3B illustrates a reflectance image of a portion of an electrical circuit having a different type of defect, namely a difficult-to-detect short, such as a shallow short 312 at location 314. Shallow shorts comprise small depositions of metal connecting between adjacent conductors, designated conductors 316 and 317. Although the amount of metal in shallow short 312 may be sufficient to electrically connect the conductors 316 and 317, because the amount of metal is small and shallow, the shallow shorts are often difficult to visualize under reflected light. Following automated optical inspection using reflective light, shallow short 312 at location 314 is indicated as a candidate defect.

It is noted that the AOI systems require considerable balance among numerous parameters in order to detect substantially all defects, while at the same time avoid excessive false calls. For example, sensitizing an AOI system to a level that facilitates detection of shallow shorts and other difficult-to-detect defects may result in excessive false detection of various non-defects like spurious bright spots on the surface of a substrate. Conversely, sensitizing an AOI system to a level that results in an acceptably low quantity of false detection calls may also result in missing at least some shallow shorts or other difficult-to-detect defects. Likewise, desensitizing inspection so as to avoid misdetection of oxidation (which is not a defect) may result, for example, in missing the detection of some real defects, such as small nick defects, on a conductor. Conversely, increasing inspection sensitivity to pick up small nick defects in a conductor may result in an undesirable excessive misdetection of oxidation as a defect.

In accordance with an embodiment of the invention, an output indicating each of the candidate defects on an electrical circuit to be inspected optionally is processed to filter out repetitive candidate defects. These include, for example, geometric candidate defects, which recur on a series of like electrical circuits. Recurring candidate defects, which recur at the same location, panel after panel, in a series of like panels of electrical circuits, may be filtered if they have been determined not to constitute an actual defect, despite a recurring geometric malformation. A methodology for filtering out recurring geometric candidate defects is described in greater detail in the present applicants concurrently filed provisional patent application No. 60/550,061, entitled Verification of Non-Recurring Defects in Pattern Inspection, the disclosure of which is incorporated herein by reference in its entirety.

An output indicating each of the candidate defects requiring verification is provided to a verification station, for example verification station 130 in FIG. 1. Referring back to FIG. 2, for each candidate defect location at least a fluorescence image is acquired, for example at verification station 130 (FIG. 1). Preferably, the fluorescence image includes the candidate defect and a small part of the area surrounding the candidate defect. A corresponding portion of a reference map, such as reference map derived from a CAM file, is also identified.

In accordance with an embodiment of the invention, contours, namely lines representing edges between conductor portions and substrate, are extracted respectively from the fluorescence image and from a corresponding reference file. In accordance with an embodiment of the invention, contours from the reference are extracted in an off-line process, and stored. Reference contours may also be used, for example, during initial inspection. Contours from the fluorescence image are compared to contours from the computer reference file. Differences between the contours of the corresponding fluorescence image and the reference, at a location generally coincident with an indication of candidate defect from optical inspection of the reflective image, are indicative of actual defects in an electrical circuit being inspected.

Methodologies for extracting contours and comparing the contours to detect defects are described, inter alia, in one or more of the following patent and patent application documents, the disclosures of which are incorporated herein by reference in their entirety: U.S. Pat. No. 5,774,772, U.S. Pat. No. 5,774,573, copending U.S. patent application publication 2003/0174877, copending U.S. patent application Ser. No. 09/633,756 (corresponding to WO0111565) and copending U.S. patent application Ser. No. 10/363,982 (corresponding to WO0221105), all of which are assigned to the present assignee, Orbotech Ltd.

Referring back to FIG. 3A, frame 320 shows a portion of a CAM image for a region surrounding candidate defect location 302 as determined from an optical inspection of a reflectance image (Frame 300). Defect 302 is a discoloration, for example from oxidation. Contours from the CAM image in frame 320 are seen in frame 322.

Frame 330 shows a fluorescence image acquired for a region generally coincident with the region seen in frame 300. In accordance with an embodiment of the present invention, frame 330 is about 500×700 pixels, and is at an resolution of about 1.5× the resolution of the image from which candidate defects are determined. Preferably a sub-region of about 350×350 pixels is utilized for optical inspection. It is noted that appropriate illumination of an electrical circuit being inspected causes the substrate to fluoresce, but not the conductors, thereby making fluorescence imaging impervious to discoloration, such as oxidation. Thus fluorescence imagery serves as an excellent tool for eliminating oxidation false calls. Consequently, in fluorescence image 330, the discoloration associated with candidate defect location 332, corresponding to location 304 in reflected image 300, is not seen.

Because the fluorescence image is insensitive to discoloration of conductors, such as oxidation, contours from the fluorescence image, seen in frame 334, are also insensitive to conductor discoloration. Comparison of contours from the reference image (frame 322) and contours from the fluorescence image (frame 334) is seen in frame 340. It is noted that at location 342, generally coincident with candidate defect location 302, comparison of the contours indicates that no defect is present.

With respect to the defect seen in FIG. 3B, frame 350 shows a portion of a CAM image for a region surrounding candidate defect 312 as determined from an optical inspection of a reflectance image (Frame 310). Contours from the CAM image in frame 350 are seen in frame 352.

Frame 360 shows a fluorescence image acquired for a region generally coincident with the region seen in frame 310. In accordance with an embodiment of the present invention, frame 360 is about 500×700 pixels, and is at an resolution of about 1.5× the resolution of the image from which candidate defects are determined. Preferably a sub-region of about 350×350 pixels is utilized for optical inspection. It is noted that appropriate illumination of an electrical circuit being inspected causes the substrate to fluoresce, but not the conductors, thereby making difficult-to-detect shorts relatively visible because of an absence of fluoresce. Consequently, shallow short 312 is clearly seen at a candidate defect location 364 in the fluorescence image generally coincident with candidate defect location 314 in frame 310. Contours corresponding to the fluorescence image in frame 360 are seen in frame 366.

Because the fluorescence image clearly contrasts shallow short 312 relative to its surrounding substrate, the defect may be readily verified. Comparison of contours from the CAM image (frame 352) and contours from the fluorescence image (frame 366) is seen in frame 370. It is noted that at location 374, generally coincident with location 314, comparison of the contours clearly indicates the presence of an actual defect.

Returning now to FIG. 2, verification is completed for each of a desired set of candidate defects. Upon completion of verification, electrical circuits are passed on for further processing. For example, an electrical circuit, in which all of the defects have been confirmed as being false defect detection, may be passed on to a further electrical circuit fabrication operation, for example, via micro-machining.

Electrical circuits in which some of the candidate defects have been verified as being actual defects, or in which automatic verification was inconclusive, may require an additional defect verification or a repair operation. In accordance with an embodiment of the invention, camera 140 is configured to additionally acquire a high quality reflectance image of a verified defect, for example at a resolution greater than the resolution of images acquired during initial inspection. Preferably the resolution of the high quality image is at least 1.5× the resolution of an image utilized for initial inspection, for example as acquired at inspection station 110. Optionally, the high quality reflectance image is acquired using various different configurations of illumination, which are optimized for the verification of selected defects. For example, some defects may be best processed when illuminated with grazing illumination.

In accordance with an embodiment of the invention, a high quality image is acquired for each candidate defect which is determined to be an actual defect or for which verification was inconclusive. The high quality image is utilized either for additional automatic image processing and optical inspection, or by a human operator to make a final determination whether the defect is an actual defect. Optionally, electrical circuits are repaired. For example, an electrical circuit in which a shallow short has been detected may be provided to a repair operator who employs a scalpel, or other equivalent device, to scrape away or otherwise remove excess conductor material causing the short.

Figure 4:
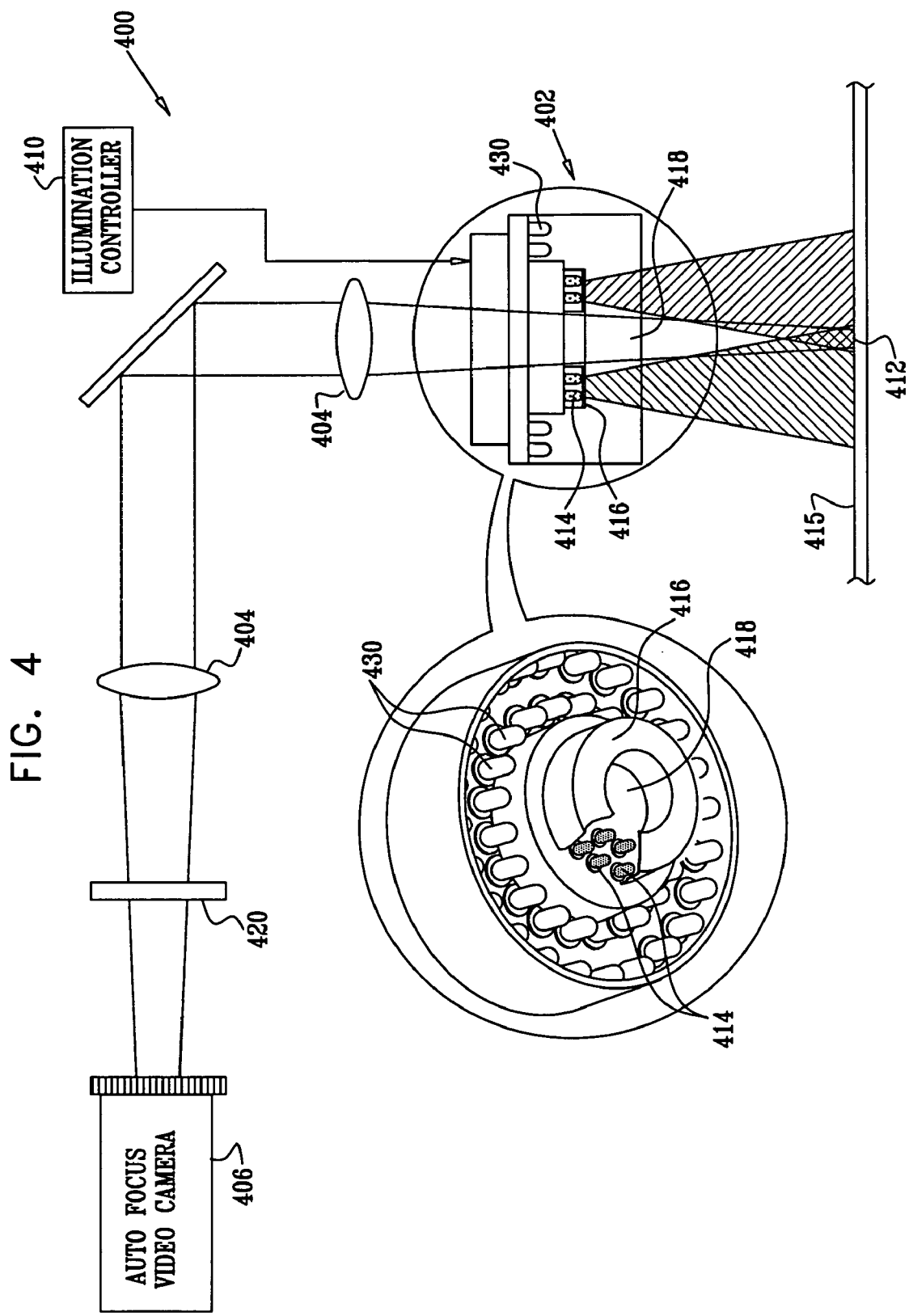
FIG. 4 is a simplified pictorial illustration of an optical head for acquiring fluorescence images employed in the system and functionality of FIG. 1.

Reference is now made to FIG. 4, which is a simplified pictorial illustration of an optical head 400 for acquiring fluorescence images employed in the system and functionality of FIG. 1. Optical head generally includes an illuminator 402, imaging and magnification optics 404 and a camera 406 arranged to acquire an image of a defect location 412 on an electrical circuit to be optically inspected. In accordance with an embodiment of the invention, illuminator 402 is driven by an illumination controller 410, configured to generate short duration illumination pulses to illuminate location 412 with short duration (within the range of between about 10-300 msec) pulsed illumination during image acquisition.

In accordance with an embodiment of the invention, illuminator 402 includes a ring light illuminator comprising a plurality of LEDs 414 arranged in at least one concentric ring to illuminate location 412 on an electrical circuit to be inspected 415 (corresponding, for example, to electrical circuit 115 in FIG. 1). LEDs 414 emit light having a primary emission in the blue, violet or ultra-violet spectrum, preferably with a wavelength of less then 410 nm. Suitable LEDs include model ETG-3UV400-30 LEDs available from ETG, Inc. of California.

As seen in FIG. 4, light from the LEDs 414 is passed through a low pass filter 416 which is operative to pass light below a selected wavelength, for example below 420 nm, but to block light in spectra above that wavelength. This ensures passage of light at 410 nm from LEDs 414. Low pass filter 416 is configured to have an opening 418 allowing location 412 to be viewed by camera 406 without filtration from low pass filter 416.

Light from LEDs 414 impinges on the electrical circuit to be inspected at location 412, and causes a substrate portion of the electrical circuit to fluoresce, emitting light having a longer wavelength, typically in the range of 480-600 nm depending on the type of material from which the substrate is fabricated.

Fluorescent light emitted by the substrate passes through opening 418 and is imaged by imaging and magnification optics 404 onto a sensor in camera 406. A high pass filter 420 allowing light above a selected wavelength, for example above 475 nm, to pass and preventing the passage of light having a wavelength below that value, is positioned upstream of camera 406. This ensures that the image acquired by camera 406 is not corrupted by stray illumination or illumination from LEDs 414 reflected by electrical circuit 415.

In accordance with an embodiment of the invention, camera 406 is a model FCB-IX47 available from Sony Corporation, providing an on-board autofocus functionality, operative to automatically focus images of location 412. In accordance with an embodiment of the invention, the arrangement of imaging and magnification optics 404 and camera 406 generally follows the teaching of U.S. patent application Ser. No. 09/570,972, now abandoned, (corresponding to PCT patent application publication WO0188592), the disclosures of which are incorporated by reference in their entirety.

In accordance with an embodiment of the invention, illuminator 402 additionally includes a second plurality of LEDs 430 arranged in a ring to illuminate location 412 from outside low pass filter 416 and having a longer wavelength than the illumination provided by LEDs 414. Illumination from LEDS 430 is, for example, generally polychromatic illumination, suitable for acquiring a high quality visual image of location 412. The high quality visual image is suitable, for example, for use in other suitable line image processing, or for use by a human operator in evaluating candidate defects at location 412. In accordance with an embodiment of the invention, auto-focus camera is operative to acquire one or more images, each image illuminated with a different configuration of illumination.

In accordance with an embodiment of the invention, the configuration of illumination is automatically selected by illumination controller 410 in response to a type of candidate defect to be verified. This information may be provided, for example, by inspection station 110 (FIG. 1), so as to optimize the image acquired by video camera 406 for use in further image processing and automatic verification, or for human review. Thus, for example, the illumination requirements for automatically verifying oxidation or shallow shorts may require a fluorescence image illuminated with violet or UV light. The illumination requirements of automatic verification for verifying some shorts may require that reflective light is provided at a grazing angle. The illumination requirements of automatic verification verifying a dish-down defect, namely a defect in which the top surface of a conductor is depressed relative to its surroundings, may require a high quality reflective image.

It will be appreciated by persons skilled in the art that the present invention is not limited to what has been particularly shown and described hereinabove. For example, various embodiments of the invention may include different combinations of sensors and control devices. The scope of the present invention includes both combinations and subcombinations of the various features described herein as well as modifications and variations thereof which would naturally occur to a person skilled in the art upon reading the foregoing description and which are not in the prior art.

The invention claimed is:

1. A method for inspecting an electrical circuit, the method comprising:
   performing a first inspection, comprising:
      optically inspecting at least a portion of an electrical circuit by detecting light reflected therefrom, while the electrical circuit is located at a first location, thus creating a first image; and
      providing a candidate defect indication indicating one or more regions of the electrical circuit determined in the first inspection to contain a possible defect, wherein the one or more regions are a subset of the inspected portion of the electrical circuit;
   performing a second inspection, comprising:
      optically inspecting only the one or more regions of the electrical circuit indicated in the first inspection, by detecting fluorescence emitted by the one or more regions, while the electrical circuit is located at a second location different from the first location, thus creating at least one second image; and
      providing a defect indication indicating defects at the one or more regions of the electrical circuit in which a defect is detected by the second inspection.

2. The method for inspecting an electrical circuit claimed in claim 1, wherein the optically inspecting at least a portion of the electrical circuit by detecting light reflected therefrom comprises scanning the electrical circuit.

3. The method for inspecting an electrical circuit claimed in claim 1, wherein the second inspection further comprises illuminating a portion of the electrical circuit with light having a wavelength of less than 420 nm.

4. The method for inspecting an electrical circuit as claimed in claim 3, wherein the second inspection further comprises providing light from a plurality of LEDs arranged in a ring, wherein the LEDs emit light in at least one of the following spectra: blue, violet, and ultra-violet.

5. The method for inspecting an electrical circuit claimed in claim 1,
   wherein the first inspection further comprises determining a location of a candidate defect from optical inspection of the first image; and
   the second inspection further comprises acquiring the second image of an area immediately surrounding the location of the candidate defect.

6. The method for inspecting an electrical circuit claimed in claim 1,
   wherein the first inspection further comprises determining a location of a candidate defect from optical inspection of said the first image; and
   the second inspection further comprises comparing a portion of the second image to a reference, wherein the portion of the second image corresponds to the location of the candidate defect.

7. The method for inspecting an electrical circuit claimed in claim 6, wherein the comparing the portion comprises:
   extracting first contours from the second image; and
   comparing the first contours to second contours obtained from the reference.

8. The method for inspecting an electrical circuit claimed in claim 1, further comprising:
   acquiring a higher quality reflectance image of the electrical circuit for at least one of: a defect and a candidate defect not conclusively determined to be a misdetection; and
   evaluating the higher quality reflectance image to make a further defect determination.

9. The method for inspecting an electrical circuit claimed in claim 1, further comprising repairing at least one candidate defect determined to be an actual defect.

10. The method for inspecting an electrical circuit claimed in claim 1, wherein the second image has a resolution that is greater than a resolution of the first image.

11. The method for inspecting an electrical circuit claimed in claim 1, wherein the first inspection is performed during a first time interval and the second inspection is performed at one or more second time intervals that are subsequent to the first time interval.

12. The method for inspecting an electrical circuit as claimed in claim 11, wherein the first time interval is temporally separate from the one or more second time intervals.

13. The method for inspecting an electrical circuit as claimed in claim 12, wherein the optically inspecting at least a portion of the electrical circuit by detecting light reflected therefrom further comprises scanning the electrical circuit and the at least one second image is created subsequent to the scanning.

14. The method for inspecting an electrical circuit claimed in claim 12, wherein the first time interval and the one or more second time intervals occur during scanning of the electrical circuit.

15. An apparatus for inspecting an electrical circuit, the apparatus comprising:
   means for performing a first inspection, comprising:
      means for optically inspecting at least a portion of an electrical circuit by detecting light reflected therefrom, while the electrical circuit is located at a first location, thus creating a first image; and
      means for providing a candidate defect indication indicating one or more regions of the electrical circuit determined in the first inspection to contain a possible defect, wherein the one or more regions are a subset of the inspected portion of the electrical circuit;

means for performing a second inspection, comprising:
means for optically inspecting only the one or more regions of the electrical circuit indicated in the first inspection, by detecting fluorescence emitted by the one or more regions, while the electrical circuit is located at a second location different from the first location, thus creating at least one second image; and
means for providing a defect indication indicating defects at the one or more regions in which a defect is detected by the second inspection.

16. The apparatus for inspecting an electrical circuit claimed in claim 15, wherein the means for performing the first inspection comprises a scanner which scans the electrical circuit.

17. The apparatus for inspecting an electrical circuit claimed in claim 15, wherein the means for performing the second inspection comprises an illuminator, which illuminates a portion of the electrical circuit where an image is to be acquired with light having a wavelength of less than 420 nm.

18. The apparatus for inspecting an electrical circuit as claimed in claim 17, wherein the illuminator comprises a plurality of LEDs arranged in a ring configuration.

19. The apparatus for inspecting an electrical circuit as claimed in claim in claim 18, further comprising a low pass filter covering the LEDs and comprising an opening, wherein the image is unfiltered by the low pass filter.

20. The apparatus for inspecting an electrical circuit claimed in claim 15, further comprising:
a defect location determiner which determines a location of a candidate defect from optical inspection of the first image; and
an image acquirer which acquires the second image from an area immediately surrounding the location of the candidate defect.

21. The apparatus for inspecting an electrical circuit claimed in claim 15, further comprising:
a defect location determiner which determines a location of a candidate defect from optical inspection of the first image; and
an image comparer which compares a portion of the second image to a reference, wherein the portion of the second image corresponds to the location of the candidate defect.

22. The apparatus for inspecting an electrical circuit claimed in claim 21, wherein the image comparer comprises:
a contour extractor which extracts first contours from the second image; and
a contour comparer which compares the first contours to second contours obtained from the reference.

23. The apparatus for inspecting an electrical circuit claimed in claim 15, further comprising:
a reflectance image acquirer which acquires a higher quality reflectance image of the electrical circuit for at least one of: a defect and a candidate defect not conclusively determined to be a misdetection; and
an image evaluator which evaluates the higher quality reflectance image and makes a further defect determination.

24. The apparatus for inspecting an electrical circuit claimed in claim 15, wherein the second image has a resolution that is greater than a resolution of the first image.

25. The apparatus for inspecting an electrical circuit claimed in claim 15, wherein the first inspection is performed during a first time interval and the second inspection is performed at one or more second time intervals that are subsequent to the first time interval.

26. The apparatus for inspecting an electrical circuit claimed in claim 15, wherein the means for performing the first inspection acquires the first image during scanning of the electrical circuit, and the means for performing the second inspection acquires the at least one second image subsequent to the scanning.

27. The apparatus for inspecting an electrical circuit claimed in claim 15, wherein the means for performing the first inspection acquires the first image during scanning of the electrical circuit, and the means for performing the second inspection acquires the at least one second image during the scanning.

28. The apparatus for inspecting an electrical circuit claimed in claim 15, wherein the first image and the at least one second image are acquired at separate intervals during scanning of the electrical circuit.

29. A method for fabricating one or more electrical circuits, the method comprising:
(a) forming an electrical circuit on a substrate;
(b) performing a first inspection, comprising:
optically inspecting at least a portion of the electrical circuit by detecting light reflected therefrom, while the electrical circuit is located at a first location, thus creating a first image; and
providing a candidate defect indication indicating one or more regions of the electrical circuit determined in said first inspection to contain a possible defect, wherein the one or more regions are a subset of the inspected portion of the electrical circuit;
(c) performing a second inspection comprising;
optically inspecting only the one or more regions of the electrical circuit indicated in the first inspection, by detecting fluorescence emitted by the one or more regions, while the electrical circuit is located at a second location different from the first location, thus creating at least one second image;
(d) providing a defect indication indicating defects at the one or more regions in which a defect is detected by the second inspection;
(e) discarding the electrical circuit in response to the defect indication at the one or more regions; and
(f) repeating operations (a) through (e).

30. The method for fabricating one or more electrical circuits claimed in claim 29, wherein the optically inspecting at least a portion of an electrical circuit by detecting light reflected therefrom comprises scanning the electrical circuit.

31. The method for fabricating one or more electrical circuits claimed in claim 29, wherein the second inspection further comprises illuminating a portion of the electrical circuit with light having a wavelength of less than 420 nm.

32. The method for fabricating one or more electrical circuits claimed in claim 29,
wherein the first inspection further comprises determining a location of a candidate defect from optical inspection of the first image; and
the second inspection further comprises acquiring the second image of an area immediately surrounding the location of the candidate defect.

33. The method for fabricating one or more electrical circuits claimed in claim 29,
   wherein the first inspection further comprises determining a location of a candidate defect from optical inspection of the first image; and
   the second inspection further comprises comparing a portion of the second image to a reference, wherein the portion of the second image corresponds to the location of the candidate defect.

34. The method for fabricating an electrical circuit claimed in claim 33, wherein the comparing the portion comprises:
   extracting first contours from the second image; and
   comparing the first contours to second contours obtained from the reference.

35. The method for fabricating one or more electrical circuits claimed in claim 29, further comprising:
   acquiring a higher quality reflectance image of the electrical circuit for at least one of: a defect and a candidate defect not conclusively determined to be a misdetection; and
   evaluating the higher quality reflectance image to make a further defect determination.

36. The method for fabricating one or more electrical circuits claimed in claim 29, further comprising repairing at least one defect.

37. The method for fabricating one or more electrical circuits claimed in claim 29, wherein the second image has a resolution that is greater than a resolution of the first image.

38. The method for fabricating one or more electrical circuits claimed in claim 29, wherein the first inspection is performed during a first time interval and the second inspection is performed at one or more second time intervals that are subsequent to the first time interval.

39. The method for fabricating one or more electrical circuits claimed in claim 29, wherein the first time interval is temporally separate from the one or more second time intervals.

* * * * *